United States Patent [19]

Gammill

[11] 4,434,296
[45] Feb. 28, 1984

[54] PROCESS FOR PREPARING INTERMEDIATES FOR ANTIATHEROSCLEROTIC COMPOUNDS

[75] Inventor: Ronald B. Gammill, Portage, Mich.

[73] Assignee: The Upjohn Company, Kalamazoo, Mich.

[21] Appl. No.: 378,687

[22] Filed: May 17, 1982

[51] Int. Cl.$^3$ ............................................ C07D 307/79
[52] U.S. Cl. .................................. 549/471; 549/387; 549/486
[58] Field of Search ........................ 549/387, 471, 486

[56] References Cited

U.S. PATENT DOCUMENTS 2,680,119 6/1954 Robertson et al. ................... 549/387
4,284,569 8/1981 Gammill ............................. 549/387

OTHER PUBLICATIONS

R. Aneja et al., A New Synthesis of Khellin, J. Sci. Industr. Res., 17B: 382–383, (1958).
R. Aneja et al., Neue Synthesen von Khellin, Chem. Ber., 93: 297–303, (1960).
R. A. Baxter et al., Furochromones, Part I, The Synthesis of Khellin, J. Chem. Soc., pp. S30–S33, (1949).
J. R. Clarke et al., Furano–Compounds, Part IX, The Synthesis of Kellin and Related Compounds, J. Chem. Soc., pp. 302–307, (1949).
O. Dann et al., Eine Neue Synthese von Khellin und Anderen Furo–2-Methyl–Chromonen, Ann. Chem. 605: 146–157, (1957).
O. Dann et al., Synthese von 2-Methyl–5.8-Dihydroxy-Furano–[3'.2': 6.7]-Chromon und von Khellin, Chem. Berg., 93: 2829–2833, (1960).
T. S. Gardner et al., The Synthesis of Khellin Derivatives, J. Org. Chem., 15: 841–849, (1950).
T. A. Geissman et al., Chromones, III, A Total Synthesis of Khellin, J. Amer. Chem. Soc., 73: 1280–1284, (1951).
V. V. S. Murti et al., A Synthesis of Kellin, J. Sci. Ind. Res. (India), 8B: 112–113, (1949).
V. V. S. Murti et al., Nuclear Oxidation in Flavones and Related Compounds Part XXIII, Proc. of the Indian Acad. of Sci., 30A: 107–113, (1949).
C. Musante, Prodotti di Scissione Alcalina Della Khellina e Loro Derivati e Trasformazione del Sistema del Furo–Cromone in Quello Del Furo–Benzoisossazolo, Gazz. Chim. Ital., 88: 910–929, (1958).
A. Mustafa, Furopyrans and Furopyrones, Chapter III, Furochromones, John Wiley and Sons, Inc., New York, pp. 102–159, (1967).
L. R. Row et al., Furanobenzopyrones: Part VII, Indian J. Chem., 5: 105–106, (1967).
A. Schonberg et al., Khellin from Visnagin, J. Amer. Chem. Soc., 73: 2960–2961, (1951).
E. Spath et al., Die Konstitution des Kellins, Chem. Ber., 71: 106–113, (1938).

*Primary Examiner*—Nicky Chan
*Attorney, Agent, or Firm*—Lawrence T. Welch; Robert A. Armitage

[57] ABSTRACT

The present specification provides a total synthesis of known intermediates useful in the synthesis of khellin and antiatherosclerotic analogs thereof. 3-Furoic acid is treated with succinic anhydride and diesterified to 3-carboxy-δ-oxo-2-furanbutanoic acid bis (alkyl ester). Following amination, cyclization and bis methylation, 6-formyl-4,7-dimethoxy-5-benzofurancarboxcyclic acid alkyl ester is prepared. This compound is then converted to known intermediates in the synthesis of khellin and analogs. Further, the present invention provides numerous novel anti-atherosclerotic 4,9-di-($C_2$–$C_4$)-alkoxyfurochromones.

1 Claim, No Drawings

PROCESS FOR PREPARING INTERMEDIATES FOR ANTIATHEROSCLEROTIC COMPOUNDS

BACKGROUND OF THE INVENTION

The present invention provides novel compositions of matter and processes for their preparation. Particularly, the present invention relates to novel chemical intermediates and associated processes for the preparation of furochromones. Most especially, the present invention provides for the preparation of novel antiatherosclerotic furochromones, particularly khellin analogs.

Khellin and related compounds are known to exert a wide variety of pharmacological effects. Recently, khellin has been reported to exhibit useful antiatherosclerotic activities. Moreover, numerous analogs of khellin likewise are known to exert useful antiatherosclerotic effects. For example, 7-methylthiomethyl-4,9-dimethoxyfurochromone is described in U.S. Pat. No. 4,284,569 as such a useful antiatherosclerotic substance.

Methods for the total synthesis of khellin are known. For example, pyrogallol has been employed as a starting material for the synthesis of furochromones such as khellin. See Clarke, J. R., et al., J. Chem. Soc., 302 (1949), Baxter, R. A., et al., J. Chem. Soc., S30 (1949), Schonberg, A., et al., J. Am. Chem. Soc., 73:2960 (1951), Murti, V. V. S., et al., Proc. of the Indian Acad. of Sci., 30A:107 (1949), and Geissman, T. A., et al., J. Am. Chem. Soc., 73:1280 (1951). Also descriptive of the synthesis of khellin are Spath, E., et al., Chem. Ber., 71:106 (1938), Dann, O., et al., Chem. Ber., 93:2829 (1960), Dann, O., et al., Ann. Chem., 605:146 (1957), and Murti, V. V. S., et al., J. Sci. Ind. Res. (India), 8B:112 (1949). See also U.S. Pat. No. 2,680,119 describing the synthesis of khellin and related compounds.

Other references describing the synthesis of intermediates useful in the preparation of khellin for analogs include: Aneja, R., et al., Chem. Ber., 93:297 (1960), Aneja, R., et al., J. Sci. Ind. Res. (India), 17B:382 (1958), Gardner, T. S., et al., J. Org. Chem., 15:841 (1950), and Rowe, L. R., et al., Indian J. Chem., 5:105 (1967).

Accordingly, the references cited above describe the preparation of 1-(6-hydroxy-4,7-dimethoxy-5-benzofuranyl)-ethanone. Also known is the related compound 6-hydroxy-4,7-dimethoxy-5-benzofurancarboxylic acid, methyl ester, described by Musante, C., Gazz. Chim. Ital., 88:910 (1958).

PRIOR ART

Methods of the total synthesis of khellin are known, as are certain chemical intermediates useful in its synthesis.

Most typically, however, the total synthesis of furochromones from benzofurans has been accomplished by utilizing a substituted benzene ring from which to synthesize the fused benzofuran ring system. See Mustafa, A., "Benzofurans," John Wiley and Sons, 1974, and Mustafa, A., "Furopyrans and Furopyrones, Chapter 3: Furochromones," John Wiley and Sons, New York, N.Y., 1967.

U.S. Pat. No. 4,284,569 provides a variety of novel antiatherosclerotic furochromones.

SUMMARY OF THE INVENTION

The present invention particularly provides:

(a) A process for preparing a compound of formula XI which comprises:

(1) reacting the lithium dianion of a compound of formula X with succinic anhydride;

(2) $C_1$-$C_4$ alkyl esterifying the resulting formula XII ketodiacid of step (1);

(3) reacting the resulting formula XIII ketodiester of step (2), wherein $R_{11}$ is $C_1$-$C_4$ alkyl, with an amide acetal of formula XIV, wherein $R_3$ and $R_4$, being the same or different, are $C_1$-$C_4$ alkyl;

(4) cyclizing of the resulting formula XV compound of step (3), wherein $R_3$, $R_4$ and $R_{11}$, are as defined above;

(5) dialkylating the resulting formula XVI benzofuran of step (4), wherein $R_{11}$ is as defined above;

(6) oxidizing the resulting formula XVII dialkoxybenzofuran of step (5), wherein $R_1$ is $C_1$-$C_4$ alkoxy and $R_{11}$ is as defined above; and (7) reducing the resulting formula XVIII compound of step (6), wherein $R_2$ and $R_{11}$ are as defined above, to the formula XI compound;

(b) A furochromone intermediate of formula I or II, wherein $R_{11}$ is $C_1$-$C_4$ alkyl; wherein $R_2$ is hydrogen or $C_1$-$C_4$ alkyl; and wherein $R_{11}$ is as defined above; wherein W is $\alpha$-H:$\beta$-H or =CH—$NR_3R_4$; wherein $R_3$ and $R_4$, being the same or different, are as defined above;

(c) A furochromone intermediate of formula III;

(d) A furochromone intermediate of formula IV, wherein $R_{11}$ is as defined above;

(e) A furochromone intermediate of formula V, wherein $R_3$, $R_4$ and $R_{11}$ are as defined as above;

(f) A furochromone intermediate of formula VI, wherein $R_{11}$ is as defined above;

(g) A furochromone intermediate of formula VII, wherein $R_{11}$ is as defined above;

(h) A furochromone intermediate of formula I or II, wherein $R_1$, $R_3$, $R_4$, and $R_{11}$ are all methyl; and (i) An anti-atherosclerotic furochromone of formula VIII wherein $R_{10}$ is $C_2$-$C_4$ alkyl; wherein $R_{12}$ is:

(1) hydrogen;
(2) $C_1$-$C_8$ alkyl;
(3) $C_2$-$C_8$ alkoxymethyl;
(4) $C_2$-$C_8$ alkylthioalkyl;
(5) trifluoromethyl;
(6) phenoxymethyl optionally substituted by chloro, fluoro, trifluoromethyl, $C_1$-$C_3$ alkyl or $C_1$-$C_3$ alkoxy;
(7) phenylthiomethyl optionally substituted by chloro, fluoro, trifluoromethyl, $C_1$-$C_3$ alkyl or $C_1$-$C_3$ alkoxy;
(8) —$CH_{21}$—$S(O)_n$—$R_{20}$, wherein n is zero, one, or 2 and $R_{20}$ is $C_1$-$C_5$ alkyl; or
(9) —$CH_2NR_8R_9$, wherein $R_8$ and $R_9$ are hydrogen, $C_1$-$C_{12}$ alkyl or wherein $R_8$ and $R_9$, taken together with N, form a saturated or unsaturated heterocyclic amine ring consisting of from 2 to 7 carbon atoms, inclusive, and zero, one, or 2 additional hereto atoms, with the proviso that said heterocyclic amine ring contains 4 to 8 atoms in the ring, said additional hetero atoms being selected from the group consisting of oxygen, nitrogen, and sulfur, said heterocyclic amine ring being optionally substituted by $C_1$-$C_4$ alkyl, $C_2$-$C_8$ alkylthiomethyl or alkoxymethyl $C_1$-$C_4$ hydroxyalkyl, or phenyl; wherein $R_{13}$ is:

(1) hydrogen;
(2) chloro, iodo, or bromo; or (3) —$CH_2$—$S(O)_n$—$R_{20}$ wherein n and $R_{20}$ are as defined above, with the proviso that $R_{13}$ is —$CH_2$—$S(O)_n$—$R_{20}$ only when $R_{14}$ is methyl.

In accordance with the method described above, there is prepared the formula XI benzofuran when $R_1$ is methoxy. This formula XI benzofuran is known to be useful in the preparation of a wide variety of antiatherosclerotic substances, including khellin and various analogs thereof. See U.S. Pat. No. 4,284,569. Similarly there are prepared the novel formula XI benzofurans when $R_1$ is $C_2$–$C_4$ alkoxy. These intermediates are useful in the preparation of novel antiatherosclerotic 4,9-di-($C_2$–$C_4$)-alkoxy-furochromones of formula VIII by means described in U.S. Pat. No. 4,284,569 for the preparation of the corresponding 4,9-dimethoxyfurochromones therein. Moreover, the manner of use of the novel 4,9-di-($C_2$–$C_4$)-alkoxy-furochromones of formula VIII in the treatment and prevention of atherosclerosis is the same as that described in U.S. Pat. No. 4,284,569 for the corresponding 4,9-dimethoxy compounds. Accordingly, the manner of the preparation and pharmacological use of these novel formula VIII compounds is incorporated herein by and reference from the description of the preparation and use in U.S. Pat. No. 4,284,569 of the anti-atherosclerotic 4,9-dimethoxyfurochromones. Among the novel formula VIII compounds herein, the 4,9-diethoxyfurochromones are preferred.

The process of the present invention is more completely understood by reference to the charts below. In these charts, $R_1$, $R_3$, $R_4$, $R_{11}$ $R_{12}$, and $R_{13}$ are as defined above. $R_5$ is:

(a) hydrogen;
(b) $C_1$–$C_8$ alkyl;
(c) $C_2$–$C_8$ alkoxymethyl;
(d) $C_2$–$C_8$ alkylthioalkyl;
(e) trifluormethyl;
(f) phenoxymethyl;
(g) phenylthiomethyl;
(h) phenoxymethyl or phenylthiomethyl, either of which is optionally substituted by one chloro, fluoro, trifluoromethyl, $C_1$–$C_3$-alkyl, or $C_1$–$C_3$-alkoxy; or
(i) $C_3$–$C_{10}$ cycloalkyl.

With regard to the substituent W in formula I, this moiety is defined as either =CH—$NR_3R_4$ or $\alpha$—H:-$\beta$—H. In the latter case reflects the fact that each of the valances of the moiety W is a hydrogen atom, one of which is attached in the $\alpha$ configuration with respect to the ring and the other which is attached in the $\beta$ configuration with respect to the ring.

The carbon atom content of various hydrocarbon containing moieties is indicated by a prefix designating the minimum and maximum number of carbon atoms in the moiety, i.e., the prefix $C_i$-$C_j$ indicates a carbon atom content of the integer "i" to the integer "j" carbon atoms, inclusive. Thus, $C_1$–$C_3$ alkyl refers to alkyl of 1–3 carbon atoms, inclusive, or methyl, ethyl, propyl, and isopropyl.

With respect to the charts, Chart A provides a method whereby the known formula XXI compound, 3-furoic acid is transformed to the highly functionalized benzofuran intermediate of formula XXVI useful in the synthesis of khellin and khellin analogs.

With further respect to chart A, the formula XXII compound is prepared from the formula XXI compound by first preparing the dianion of the formula XXI compound. See Knight, D. W., et al., J. Chem. Soc. Perkins, 1125 (1981), and references cited therein. Accordingly, this dianion is generated by treatment of the formula XXII compound with two equivalents of lithium diisopropylamide at low temperature, e.g., −78° C. At this temperature the resulting dianion is stable for several hours.

The dianion is then transformed to the formula XXII compound by treatment with succinic anhydride.

The resulting formula XXII is then esterified to the formula XXIII compound by conventional means. For example, an etherial diazoalkane is employed or, for larger scale synthesis, an alkanol in hydrochloric acid is useful.

The formula XXIII compound is then converted to the formula XXIV compound by reaction at elevated temperature with an N,N-dialkylformamide dimethylacetal. Preferably, N,N-dimethylformamide dimethylacetal is employed at temperatures in excess of 80° C. For example, reaction at 100° C. for 2 hr yields the formula XXIV compound.

Although this reaction preceeds in relatively high yield at elevated temperature, a less complex mixture of products is obtained by reacting the formula XXIII with the desired formamide for prolonged periods, i.e., up to a week. The optimal conditions for the preparation of the formula XXIV compound by this method are the stirring of the formula XXIII reactant in neat N,N-dimethylformamide dimethylacetal employing a trace of p-toluenesolfonic acid. Alternatively base catalysis is employed using alkoxides, e.g., potassium tertbutoxide in an organic solvent.

The formula XXV compound is then prepared from the formula XXIV compound by a Dieckmann cyclization. Preferably the cyclization occurs under basic conditions, e.g., preferably using potassium tertbutoxide in organic solvent, followed by an acid quench. Suitable organic solvents include benzene and tert-butanol, although the preferred solvent is tetrahydrofuran.

Finally, the formula XXVI compound of Chart A is prepared from the formula XXV compound by alkylation. Alkylation can be accomplished quantitatively by treatment of the formula XXV reactant with an alkyliodide in potassium carbonate.

Chart B provides a method whereby the formula XXXI compound, prepared as the formula XXVI compound of Chart A is converted to formula XXXIII intermediate, a compound known to be useful in the preparation of both khellin and analogs thereof. In accordance with the procedure of Chart B, the formula XXXI compound is transformed to the formula XXXII compound by a Baeyer Villager oxidation. For this oxidation, m-chloroperbenzoic acid is employed at ambient temperature in an organic solvent. Tetrahydrofuran or isopropanol represents the preferred solvent for undertaking this oxidation.

Finally, the formula XXXII compound is transformed into the formula XXXIII compound by conversion of the ester group to a methyl ketone. For this purpose a Grignard reagent in the presence of a tertiary amine is employed according to the method of Kikkawa, I., and Yorifuji, T., Synthesis, 887 (1981).

Chart C provides a summary of the method by which the formula XLI compound, prepared as the formula XXXIII compound of Chart B, is transformed to khellin or analogs thereof. The procedures of Chart C are, for example, known in the art from U.S. Pat. No. 4,284,569, wherein Charts A-D of that patent describe the synthesis of the various formula XLII and formula XLIII compounds from the formula XLI starting material.

Accordingly, the charts herein provide a description of the preparation and use of the novel process and compounds of the present invention.

DESCRIPTION OF THE PREFERRED EMBODIMENTS

The present disclosure is more fully understood by the operation of the following examples:

EXAMPLE 1

3-Carboxy-γ-oxo-2-furanbutanoic acid (Formula XXII)

Refer to Chart A

Diisopropylamine (202 g) is added to a flame dried 3 neck flask with a mechanical stirrer, droping funnel and nitrogen inlet. To this amine is added tetrahydrofuran (THF, 600 ml). This solution is then cooled to −78° C. and n-butyllithium (128 g in hexane, 1.6 m) added over 20 min. After complete addition of the n-butyllithium the reaction is stirred for 2.5 h, the last hour of which, the reaction vessel was only 25% submerged in the dry ice bath. At this point, the lithium diisopropylamine (LDH) separates from solution. Two liters of THF are added and a homogeneous solution developes. The reaction is then completely submerged in the dry ice bath and the 3-furoic acid, formula XXI (100 g), in THF (600 ml) is added over 30 minutes. After complete addition of 3-furoic acid the reaction is stirred an additional two hours. At this point, succinic anhydride (100 g) in THF (800 ml) is rapidly added via the addition funnel. A solid almost immediately begins to separate from solution. As the reaction warms to room temperature, quenching is effected with 2 N hydrochloric acid (3 liters). The entire reaction is poured into a portable separatory funnel. The organic layer is separated and the aqueous back extracted with trichloromethane (3 liters). The organic extracts are dried ($MgSO_4$) and solvent removed in vacuo to give an off-white solid which after an ether wash afforded 120 g of pure white title, mp 181°-200° C. IR absorption ($cm^{-1}$) absorptions are observed at 3140, 3120, 2740, 2640, 1740, 1705, 1630, 1615, 1570, 1330, 1270, 1215, 1165, 890 and 775. $^1$H-NMR absorptions (δ, $CDCl_3$) are observed at 7.73, 7.05, 3.38 and 2.71. Mass spectral peaks are observed at 212, 194, 176, 167, 150, 149, 140, 139, 95, 55 and 39.

EXAMPLE 2

3-Carboxy-γ-oxo-2-furanbutanoic acid bis (methyl ester) (Formula XXIII: $R_{11}$ is methyl)

Refer to Chart A

The formula XXII product of Example 1 (170 mg) is suspended in trichloromethane (10 ml) and treated with excess diazomethane. When TLC (5% $EtOAc/CHCl_3$) indicated complete conversion to the bismethyl ester, the trichloromethane is removed in vacuo to yield 211 mg of crude product which was chromatographed (Merck B, 5% $EtOAc/CHCl_3$) to yield 211 mg of the pure title product as a colorless oil.

Silica Gel TLC $R_f$ is 0.39 in 5% ethyl acetate in trichloromethane. IR absorptions ($cm^{-1}$) are observed at 3050, 1735, 1695, 1590, 1480, 1440, 1400, 1360, 1305, 1280 and 1160. $^1$H-NMR absorptions (δ, $CDCl_3$) are observed at 7.5, 6.83, 3.90, 3.71, 3.30, and 2.75. Mass spectral peaks are observed at 240, 208, 181, 176, 153, 149, 123, 95, 55 and 38.

EXAMPLE 3

β-[(Dimethylamino)methylene]-3-(methoxycarbonyl)-γ-oxo-2-furanbutanoic acid bis (methyl ester) (Formula XXIV: $R_3$, $R_4$ and $R_{11}$ are all methyl)

Refer to Chart A

The formula XXIII product of Example 2 (500 mg) and N,N-dimethylformamide dimethylacetal (230 mg) are heated neat at 100° C. for 1 hour. The reaction is then cooled to room temperature and excess acetal and methanol are removed in vacuo. The resulting brown oil is chromatographed (eluting with 5% methanol in ethyl acetate) to yield 280 mg of title product as a yellow oil.

Silica Gel TLC $R_f$ is 0.4 in 5% methanol in ethyl acetate. IR absorptions ($cm^{-1}$) are observed at 3120, 2950, 1725, 1640, 1560, 1430, 1405, 1390, 1320 and 1160. NMR absorptions (δ, $CDCl_3$) are observed at 7.45, 6.95, 6.73, 3.82, 3.68 and 3.07. Mass spectral peaks are observed at 295, 263, 264, 237, 236, 218, 182, 153, 142 and 139.

EXAMPLE 4

6-Formyl-4,7-dihydroxy-5-benzofurancarboxylic acid methyl ester (Formula XXV: $R_{11}$ is methyl)

Refer to Chart A

A. (Preparation 1) Potassium metal (50 mg, 1.28 mmol) is added to tert-butanol (5 ml) under nitrogen with stirring. After the potassium metal has dissolved the formula (190 mg), in tert-butanol (5 ml) is added at room temperature. As the drops of diester hit the solution, a deep red color developes. This color slowly fades to yellow with time. After complete addition of the formula XXIV product of Example 3, the reaction is stirred an additional hour and then diluted with water. The reaction acidified with 2 N HCl and was extracted with diethyl ether and then with trichloromethane. The combined organic extracts are dried ($MgSO_4$) and solvent removed in vacuo to yield a brown solid which after chromatography affords 40 mg of title product.

Silica Gel TLC $R_f$ is 0.50 in 5% $EtOAc/CHCl_3$. IR absorptions ($cm^{-1}$) are observed at 3500, 2600, 1670, 1640, 1580, 1430, 1360, 1300, 1250. NMR absorptions (δ, $CDCl_3$) are observed at 10.5, 7.81, 7.0 and 4.0. Mass spectral peaks are observed at 236, 205, 204, 203, 176, 149, 148, 147, 119 and 63.

B. (Preparation 2) Potassium tert-butoxide (319 mg) is added to 20 ml of dry THF under nitrogen. This mixture is then cooled to −78° C. and the formula XXIV starting material (420 mg) in THF (15 ml) added via syringe pump at a rate of 0.23 ml/min. A deep red color developes. After complete addition the reaction is stirred an additional 30 minutes and then the reaction is quenched at −78° C. by the addition of 2 N HCl. The reaction is then warmed to room temperature and poured into a separatory funnel. Then 2 N HCl (50 ml) is added and the reaction was extracted with ethyl acetate (3×75 ml). The aqueous layer is then extracted with trichloromethane. The combined organic extracts are dried ($MgSO_4$) and solvent removed in vacuo to 340 mg of a brown solid. This solid is chromatographed over silica gel eluting with 5% ethyl acetate in trichloromethane to yield 200 mg of title product.

EXAMPLE 5

6-Formyl-4,7-dimethoxy-5-benzofurancarboxylic acid methyl ester (Formula XXVI: $R_1$ and $R_{11}$ are methyl)

Refer to Chart A

6-Formyl-4,7-dihydroxy-5-benzofurancarboxylic acid methyl ester (Example 4, 4.70 g) is added to acetone (100 ml) followed by addition of methyliodide (5.65 g) and potassium carbonate (5.0 g). The resulting mixture is heated at reflux for 24 hr. The reaction is cooled to room temperature and trichloromethane (100 ml) is added. Water (200 ml) is added. The organic layer is separated and the aqueous layer back extracted with trichloromethane (2×75 ml). The combined organic layer is dried (MgSO$_4$) and solvent removed in vacuo to yield a yellow oil. Chromatography over 100 g of silica gel eluting with 5% ethyl acetate in trichloromethane affords 5.2 g of title product as a pale yellow oil that slowly crystallized on standing. A pure product is prepared by recrystallization from methanol, mp 89.9°–90.8° C.

Silica Gel TLC $R_f$ is 0.44 in 5% EtOAc/CHCl$_3$. IR absorptions (cm$^{-1}$) are observed at 1730, 1680, 1600, 1470, 1440, 1390, 1340, 1305, 1290, 1060, 980 and 930. NMR absorptions ($\delta$, CDCl$_3$) are observed at 10.4, 7.83, 6.97, 4.38 and 3.98. Mass spectral peaks are observed at 264, 249, 236, 233, 221, 205, 203, 189 and 147.

EXAMPLE 6

6-Hydroxy-4,7-dimethoxy-5-benzofurancarboxylic acid, methyl ester (Formula XXXII: $R_1$ and $R_{11}$ are methyl)

Refer to Chart B

A. (Procedure I) A solution of 6-Formyl-4,7-dimethoxy-5-benzofurancarboxylic acid, methyl ester (Example 5, 104.0 mg) in isopropanol (8.0 ml) is treated with 85% m-chloroperbenzoic acid (MCPBA, 188 mg) at ambient temperature and stirred overnight. The solvent is removed on the rotary evaporator and the residue is taken up into 10% aqueous sodium carbonate (10 ml) and diethyl ether (10 ml). After stirring for 30 minutes the layers are separated and the aqueous is extracted with additional diethyl ether (1×20 ml). The ether extracts are combined and dried (MgSO$_4$). The residue is chromatographed (20 g silica gel) eluting with 20% ethyl acetate in isomeric hexanes (Skellysolve B) to provide 63.2 mg of white solid, title product, mp 82°–4° (yield 63%).

B. (Procedure II) When the reaction is repeated as above substituting THF as the solvent, 101.5 mg of starting material and 184 mg of MCPBA yields 30.0 mg of pure product, mp 82°–84°.

EXAMPLE 7

1-(6-Hydroxy-4,7-dimethoxy-5-benzofuranyl)-ethanone (Formula XXXIII: $R_1$ is methyl)

A. A 100 ml 3 neck flask is oven dried and cooled under nitrogen. Benzene (10 ml) is placed in the flask followed by methyl magnesium bromide (2.9 M in diethyl ether, 2.0 ml). To that solution is added dry triethylamine (2.45 ml) and the resulting mixture is cooled to 8°–10°. A solution of 6-hydroxy-4,7-dimethoxy-5-benzofurancarboxylic acid methyl ester (Example 6, 250 g) in dry benzene (15 ml) is then added dropwise to the cold reaction mixture over a 15 min period. The resulting mixture is yellow; the ice bath is removed and stirring continued at ambient temperature for 6.5 hours.

B. The reaction mixture is then cooled in ice and quenched by the addition of saturated ammonium chloride (10 ml). Diethyl ether (40 ml) is next added, along with 2 N HCl (30 ml). The layers are separated, the ether layer dried (MgSO$_4$) and concentrated to an oil. This crude mixture was heated with 10 ml of 5% aqueous potassium hydroxide for 2 hr. The mixture is then carefully acidified (6 N HCl) and extracted with ethyl acetate (3×25 ml). The combined organic extracts are washed with saturated sodium bicarbonate (2×20 ml) and dried (MgSO$_4$). Evaporation of the solvent yields 0.13 g of yellow solid which is chromatographed (on silica gel eluting with 20% ethyl acetate in Skellysolve B SSB eluent) to afford 0.128 g of title product. Recrystallization of that material (hexane/ethyl acetate, 10:1) yields 85 mg of pure, bright yellow title product as a solid.

The product of Example 7 is identical to the product of Example 1 of U.S. Pat. No. 4,284,569 and is accordingly useful for the preparation of khellin and analogs thereof, e.g., see Examples 2–21 of U.S. Pat. No. 4,284,569.

EXAMPLE 8

7-methylthiomethyl-4,9-diethoxyfurochromone (Formula XLIII: $R_1$ is ethyl, $R_{12}$ is methylthiomethyl, and $R_{13}$ is methyl)

Refer to Chart C

A. 6-Formyl-4,7-dihydroxy-5-benzofurancarboxylic acid methyl ester (Example 4, 4.70 g) is added to acetone (100 ml) followed by addition of ethyliodide (5.80 g) and potassium carbonate (5.0 g). The resulting mixture is heated at reflux for 24 hr. The reaction is cooled to room temperature and trichloromethane (100 ml) is added. Water (200 ml) is added. The organic layer is separated and the aqueous layer back extracted with trichloromethane (2×75 ml). The combined organic layer is dried (MgSO$_4$) and solvent removed in vacuo to yield a residue. Chromatography over 100 g of silica gel eluting with 5% ethyl acetate in trichloromethane affords product.

B. A solution of 6-Formyl-4,7-diethoxy-5-benzofurancarboxylic acid, methyl ester (part A, 105.0 mg) in isopropanol (8.0 ml) is treated with 85% m-chloroperbenzoic acid (m-CPBA, 188 mg) at ambient temperature and stirred overnight. The solvent is removed on the rotary evaporator and the residue is taken up into 10% aqueous sodium carbonate (10 ml) and diethyl ether (10 ml). After stirring for 30 minutes the layers are separated and the aqueous is extracted with additional diethyl ether (1×20 ml). The ether extracts are combined and dried (MgSO$_4$). The residue is chromatographed (20 g silica gel) eluting with 20% ethyl acetate in isomeric hexanes (Skellysolve B) to provide product.

C. A 100 ml 3 neck flask is oven dried and cooled under nitrogen. Benzene (10 ml) is placed in the flask followed by methyl magnesium bromide (2.9 M in diethyl ether, 2.0 ml). To that solution is added dry triethylamine (2.45 ml) and the resulting mixture is cooled to 8°–10°. A solution of 6-hydroxy-4,7-dimethoxy-5-benzofurancarboxylic acid methyl ester (part B, 250 g) in dry benzene (15 ml) is then added dropwise to the cold reaction mixture over a 15 min period. The ice bath is removed and stirring continued at ambient temperature for 6.5 hours.

D. The reaction mixture of part C is then cooled in ice and quenched by the addition of saturated ammonium chloride (10 ml). Diethyl ether (40 ml) is next added, along with 2 N HCl (30 ml). The layers are separated, the ether layer dried (MgSO₄) and concentrated to an oil. This crude mixture was heated with 10 ml of 5% aqueous potassium hydroxide for 2 hr. The mixture is then carefully acidified (6 N HCl) and extracted with ethyl acetate (3×25 ml). The combined organic extracts are washed with saturated sodium bicarbonate (2×20 ml) and dried (MgSO₄). Evaporation of the solvent yields a residue which is chromatographed (on silica gel eluting with 20% ethyl acetate in Skellysolve B eluent) to afford product.

E. To sodium hydride (20.1 g of a 50% dispersion in oil) and tetrahydrofuran (20 ml freshly distilled from lithium aluminum hydride), combined under a nitrogen atmosphere to form a slurry, are added dropwise a mixture of the product of part D (56 g), ethyl 2-(methylthio)-acetate (26.4 g) and dry tetrahydrofuran (50 ml). After the addition is complete (1.5 hr) the reaction mixture is then heated on a steam bath for 15 min and cooled to ambient temperature. Thereupon excess sodium hydride is destroyed by careful addition of ice and water (300 ml). Washing with diethyl ether (600 ml) yields an aqueous layer which is diluted with methanol (100 ml) and concentrated hydrochloric acid (75 ml). This mixture is then refluxed for 45 min and thereupon allowed to cool to ambient temperature. Upon extraction with methylene chloride (600 ml) the organic extracts are dried and concentrated under reduced pressure to yield pure title product.

FORMULAS

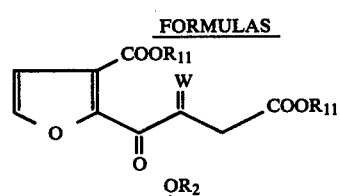  I

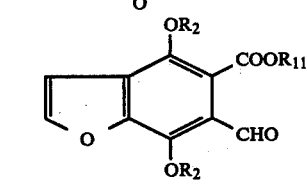  II

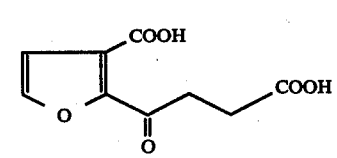  III

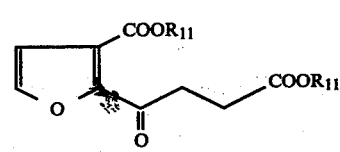  IV

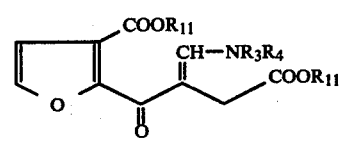  V

-continued
FORMULAS

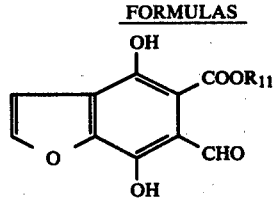  VI

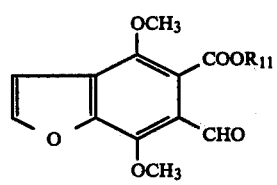  VII

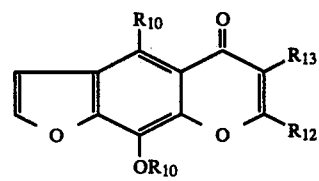  VIII

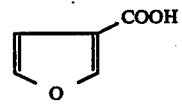  X

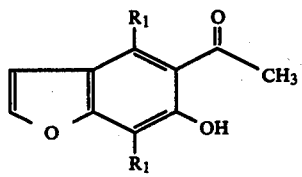  XI

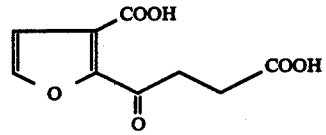  XII

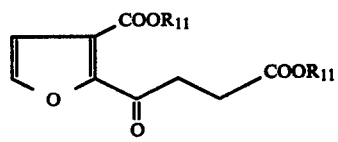  XIII

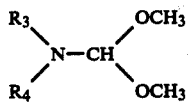  XIV

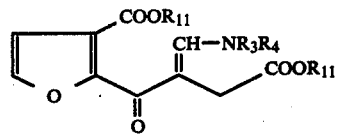  XV

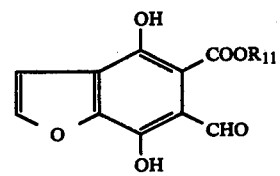  XVI

-continued
FORMULAS

XVII

[Structure: benzofuran with R₁ at 4-position, COOR₁₁ at 5-position, CHO at 6-position, R₁ at 7-position]

XVIII

[Structure: benzofuran with R₁, COOR₁₁, OH, R₁ substituents]

CHART A

[Structure: furan-3-carboxylic acid]

↓

[Structure: furan with COOH and 2-(3-carboxypropanoyl) group]

↓

[Structure: furan with COOR₁₁ and 2-(3-(COOR₁₁)propanoyl) group]

↓

[Structure: furan with COOR₁₁ and =CH-NR₃R₄ enaminone, COOR₁₁]

↓

[Structure: 4,7-dihydroxybenzofuran with COOR₁₁ and CHO]

↓

-continued
CHART A

XXVI

[Structure: benzofuran with R₁, COOR₁₁, CHO, R₁]

CHART B

XXXI

[Structure: benzofuran with R₁, COOR₁₁, CHO, R₁]

↓

XXXII

[Structure: benzofuran with R₁, COOR₁₁, OH, R₁]

↓

XXXIII

[Structure: benzofuran with R₁, C(O)CH₃, OH, R₁]

CHART C

XLI

[Structure: benzofuran with R₁, C(O)CH₃, OH, R₁]

↓

XLII

[Structure: benzofuran with R₁, -C(O)CH₂C(O)R₅, R₁]

↓

-continued
CHART C

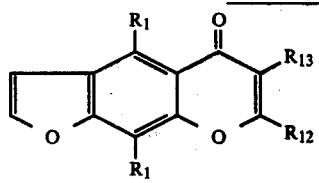

I claim:
1. A process for preparing a compound of formula XI

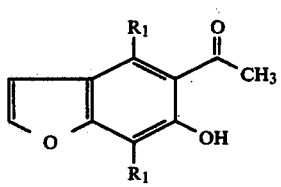

wherein $R_1$ is $C_1$-$C_4$ alkyl which comprises:
(1) reaching the lithium dianion of a compound of formula X

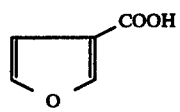

with succinic anhydride;
(2) $C_1$-$C_4$ alkyl esterifying the resulting formula XII

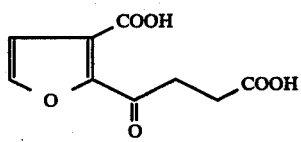

ketodiacid of step (1);
(3) reacting the resulting formula XIII

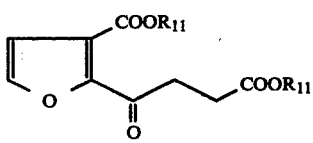

ketodiester of step (2), wherein $R_{11}$ is $C_1$-$C_4$ alkyl, with an amide acetal of formula XIV

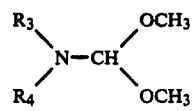

wherein $R_3$ and $R_4$, being the same or different, are $C_1$-$C_4$ alkyl;
(4) cyclizing of the resulting formula XV

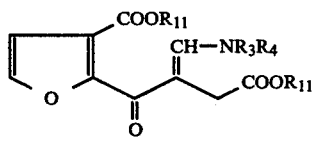

compound of step (3), wherein $R_3$, $R_4$, and $R_{11}$ are as defined above;
(5) di-($C_1$-$C_4$)-alkylating the resulting formula XVI

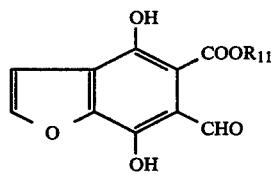

benzofuran of step (4);
(6) oxidizing the resulting formula XVII

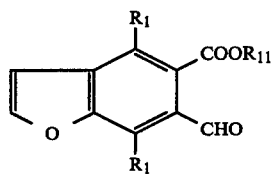

compound of step (5), and
(7) reducing the resulting formula XVIII

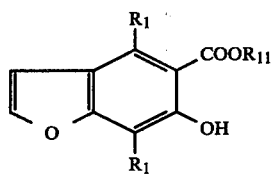

compound of step (6) to the formula XI compound.

* * * * *